(12) United States Patent
Coman et al.

(10) Patent No.: US 10,551,521 B2
(45) Date of Patent: Feb. 4, 2020

(54) MAGNETIC RESONANCE PULSE SEQUENCES AND PROCESSING

(71) Applicants: Radu Coman, Hannover (DE); Martin Blanz, Celle (DE); Holger Tietjen, Hannover (DE)

(72) Inventors: Radu Coman, Hannover (DE); Martin Blanz, Celle (DE); Holger Tietjen, Hannover (DE)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 543 days.

(21) Appl. No.: 15/151,672

(22) Filed: May 11, 2016

(65) Prior Publication Data

US 2016/0334533 A1 Nov. 17, 2016

Related U.S. Application Data

(60) Provisional application No. 62/160,401, filed on May 12, 2015.

(51) Int. Cl.
*G01V 3/32* (2006.01)
*G01R 33/561* (2006.01)

(52) U.S. Cl.
CPC ............ *G01V 3/32* (2013.01); *G01R 33/5615* (2013.01)

(58) Field of Classification Search
CPC ... G01V 3/14; G01V 3/32; G01V 3/38; G01N 24/08; G01N 24/081; G01R 33/448; G01R 33/5615; G01R 33/5617; G01R 33/56554

USPC .......................... 324/300–322; 600/407–435; 382/128–131
See application file for complete search history.

(56) References Cited

U.S. PATENT DOCUMENTS

| 4,318,043 | A | * | 3/1982 | Crooks | .................. | G01R 33/54 |
| | | | | | | 324/309 |
| 4,502,007 | A | * | 2/1985 | Mee | ....................... | G01R 33/50 |
| | | | | | | 324/300 |
| 5,023,551 | A | | 6/1991 | Kleinberg et al. | | |

(Continued)

OTHER PUBLICATIONS

Akkurt, et al. "Enhanced Diffusion Expanding the Range of NMR Direct HydroCarbon-Typing Applications"; SPWLA 39th Annual Logging Symposium, May 26-29, 1998; 14 pages.

(Continued)

*Primary Examiner* — Steven L Yeninas
(74) *Attorney, Agent, or Firm* — Cantor Colburn LLP (57) ABSTRACT

A nuclear magnetic resonance (NMR) apparatus includes a carrier configured to be deployed in a borehole, a magnet assembly configured to generate a static magnetic field in an earth formation, and at least one transmitting assembly configured to generate an oscillating magnetic field in a volume of interest within the formation. The apparatus also includes a pulse generator configured to apply a direct-echo pulse sequence to the at least one transmitting assembly, the direct-echo pulse sequence having a plurality of successive pulses including a first pulse and a second pulse configured to generate a first direct NMR echo, and a third pulse, the third pulse selected to at least partially separate a stimulated NMR echo from a second direct NMR echo occurring after the third pulse. The apparatus further includes at least one receiving assembly configured to detect the first and second direct echoes of an NMR echo train.

18 Claims, 5 Drawing Sheets

(56) References Cited

U.S. PATENT DOCUMENTS

| | | | |
|---|---|---|---|
| 5,486,762 A | 1/1996 | Freedman et al. | |
| 5,798,643 A | 8/1998 | Werthner | |
| 6,051,973 A | 4/2000 | Prammer | |
| 6,069,477 A * | 5/2000 | Chen | G01N 24/081 324/303 |
| 6,121,774 A * | 9/2000 | Sun | G01N 24/081 324/300 |
| 6,163,153 A * | 12/2000 | Reiderman | G01N 24/08 324/303 |
| 6,215,304 B1 * | 4/2001 | Slade | G01N 24/081 324/303 |
| 6,331,775 B1 * | 12/2001 | Thern | G01N 24/081 324/303 |
| 6,392,409 B1 | 5/2002 | Chen | |
| 6,498,484 B1 | 12/2002 | Sun et al. | |
| 6,600,315 B1 | 7/2003 | Heaton et al. | |
| 6,891,369 B2 * | 5/2005 | Hurlimann | G01N 24/081 324/303 |
| 7,301,337 B2 | 11/2007 | Beard | |
| 7,528,600 B2 | 5/2009 | Sen et al. | |
| 2003/0016013 A1 * | 1/2003 | Kruspe | G01R 33/50 324/303 |
| 2003/0071620 A1 * | 4/2003 | Reiderman | G01R 33/4608 324/314 |
| 2003/0085702 A1 * | 5/2003 | Freed | G01R 33/4625 324/303 |
| 2003/0132749 A1 | 7/2003 | Speier et al. | |
| 2004/0008027 A1 * | 1/2004 | Prammer | G01N 24/081 324/303 |
| 2004/0257075 A1 | 12/2004 | An et al. | |
| 2005/0104587 A1 | 5/2005 | Akkurt | |
| 2008/0024128 A1 * | 1/2008 | Song | G01N 24/081 324/307 |
| 2010/0023786 A1 | 1/2010 | Liberman | |
| 2010/0237865 A1 | 9/2010 | Stemmer | |
| 2010/0283460 A1 | 11/2010 | Kruspe et al. | |
| 2013/0200890 A1 | 8/2013 | Hursan | |
| 2014/0055134 A1 * | 2/2014 | Fordham | G01R 33/4818 324/309 |
| 2015/0022202 A1 | 1/2015 | Song et al. | |
| 2015/0241541 A1 | 8/2015 | Blanz et al. | |
| 2016/0047936 A1 | 2/2016 | Ali et al. | |
| 2016/0116629 A1 | 4/2016 | Coman et al. | |
| 2016/0320519 A1 | 11/2016 | Blanz et al. | |
| 2017/0153352 A1 * | 6/2017 | Ganssle | G01N 15/088 |
| 2017/0184755 A1 | 6/2017 | Coman | |

OTHER PUBLICATIONS

Coates, et al.; "NMR Logging Principles & Applications"; Halliburton Energy Services; (1999); Part one; 131 pages.
Coates, et al.; "NMR Logging Principles & Applications"; Halliburton Energy Services; (1999); Part Two; 116 pages.
Dodge, et al.; "A Case Study Demonstrating How NMR Logging Reduces Completion Uncertainties in Low Porosity, Tight Gas Sand Reservoirs"; SPWLA 39th Annual Logging Symposium, May 26-29, 1998; 14 pages.
Dunn, et al.; "NMR Relaxation";Nuclear Magnetic Resonance Petrophysical and Logging Applications; PERGAMON (2002). 10 pages.
Goelman, et al.; "The CPMG Pulse Sequence in Strong Magnetic Field Gradients with Applications to Oil-Well Logging"; Journal of Magnetic Resonance Series A 113, 11-18 (1995); 8 pages.
International Search Report and the Written Opinion of the International Searching Authority, or the Declaration; PCT/US2016/031819; dated Sep. 13, 2016; 7 pages.
International Search Report and the Written Opinion of the International Searching Authority, or the Declaration; PCT/US2016/064680; dated Mar. 20, 2017; 14 pages.
Prammer, et al.; "Measurements of Clay-Boound Water and Total Porosity by Magnetic Resonance Logging"; SPE 36522; (1996); 10 pages.
Coman, et al.; "Improved NMR logging Approach to Simultaneously Determine Porosity, T2 and T1"; SPE, Society of Petroleum Engineers; Sep. 2015; pp. 1-27.
PetroWiki; "Porosity Determination with NMR Logging" Society of Petroleum Engineers (SPE International), Jun. 24, 2015; pp. 1-7.
Freedman, "Advances in NMR Logging"; Jan. 2006, JPT, pp. 60-66, (Year 2006).
Moritz; "NMR Tools Afford New Logging Choices"; Apr. 17, 2000, Oil & Gas Joournal, pp. 1-16. (Year 2000).
David Allen et al. (Schlumberger); "How to Use Borehole Nuclear Magnetic Resonance"; Oilfield Review, pp. 34-57. (Year 1997).
Xie et al.; "Advanced Fluid-Typing Methods for NMR logging"; Jan. 14, 2010, Pet Sci (2011), pp. 163-169. (Year 2010).
Non-Final Office Action for U.S. Appl. No. 14/979,998, filed Dec. 28, 2015, Confirmation No. 6860, dated Mar. 12, 2019, 15 pgs.

* cited by examiner

MAGNETIC RESONANCE PULSE SEQUENCES AND PROCESSING

CROSS REFERENCE TO RELATED APPLICATIONS

This application claims the benefit of an earlier filing date from U.S. Provisional Application Ser. No. 62/160,401 filed May 12, 2015, the entire disclosure of which is incorporated herein by reference.

BACKGROUND

Understanding the characteristics of geologic formations and fluids located therein is important for effective hydrocarbon exploration and production. Formation evaluation relies on accurate petrophysical interpretation derived from a diverse set of logging technologies. One such technology, nuclear magnetic resonance (NMR), can be used to estimate formation characteristics such as mineralogy-independent porosity and permeability of rocks, to perform fluid typing and determine fluid volumes, and to estimate fluid characteristics such as viscosity.

Processing results from NMR operations have indicated that porosity overcall is a significant problem in formations with short relaxation time $T_2$ (e.g., on the order of milliseconds (ms)) if $T_1$ is greater than $T_2$. For example, NMR measurements in formations having shale intervals have exhibited significant porosity overcall (in the order of 20 percent) in some shale intervals, even though porosity in other regions was found to be correct.

SUMMARY

An embodiment of a nuclear magnetic resonance (NMR) apparatus for estimating properties of an earth formation downhole includes a carrier configured to be deployed in a borehole in the earth formation, a magnet assembly disposed in the carrier and configured to generate a static magnetic field in the formation, and at least one transmitting assembly disposed in the carrier and configured to generate an oscillating magnetic field in a volume of interest within the formation. The apparatus also includes a pulse generator configured to apply a direct-echo pulse sequence to the at least one transmitting assembly, the direct-echo pulse sequence having a plurality of successive pulses, the plurality of successive pulses including a first pulse and a second pulse configured to generate a first direct NMR echo, and a third pulse, the third pulse selected to at least partially separate a stimulated NMR echo from a second direct NMR echo occurring after the third pulse. The apparatus further includes at least one receiving assembly disposed in the carrier and configured to detect the first and second direct NMR echoes of an NMR echo train.

An embodiment of a method of estimating properties of an earth formation downhole includes deploying a carrier into a borehole in the earth formation, generating a static magnetic field in a volume of interest within the formation by a magnet assembly disposed in the carrier, and emitting pulses of an electromagnetic signal, by at least one transmitting assembly disposed in the carrier, into the volume of interest to generate an oscillating magnetic field, the pulses emitted as a direct-echo pulse sequence having a plurality of successive pulses, the plurality of successive pulses including a first pulse and a second pulse configured to generate a first direct NMR echo, and a third pulse, the third pulse selected to at least partially separate a stimulated NMR echo from a second direct NMR echo occurring after the third pulse. The method also includes estimating a property of the volume of interest by a processor based on amplitudes of at least the first and second direct NMR echoes of an NMR echo train resulting from the pulse sequence.

BRIEF DESCRIPTION OF THE DRAWINGS

The subject matter which is regarded as the invention is particularly pointed out and distinctly claimed in the claims at the conclusion of the specification. The foregoing and other features and advantages of the invention are apparent from the following detailed description taken in conjunction with the accompanying drawings in which:

DETAILED DESCRIPTION

Methods, systems and apparatuses for measuring characteristics of an earth formation using magnetic resonance techniques are described herein. Embodiments of nuclear magnetic resonance (NMR) apparatuses, systems and methods utilize a direct-echo pulse sequence that is effective in reducing or eliminating errors in measurement results due to previously unconsidered second-order stimulated echo effects. The second-order stimulated echo effect is significant, for example, in formations with fast relaxation times (e.g., shale, heavy oil) and a $T_1/T_2$ ratio>1. The direct-echo pulse sequence is effective especially for providing an accurate microporosity.

Figure 1:
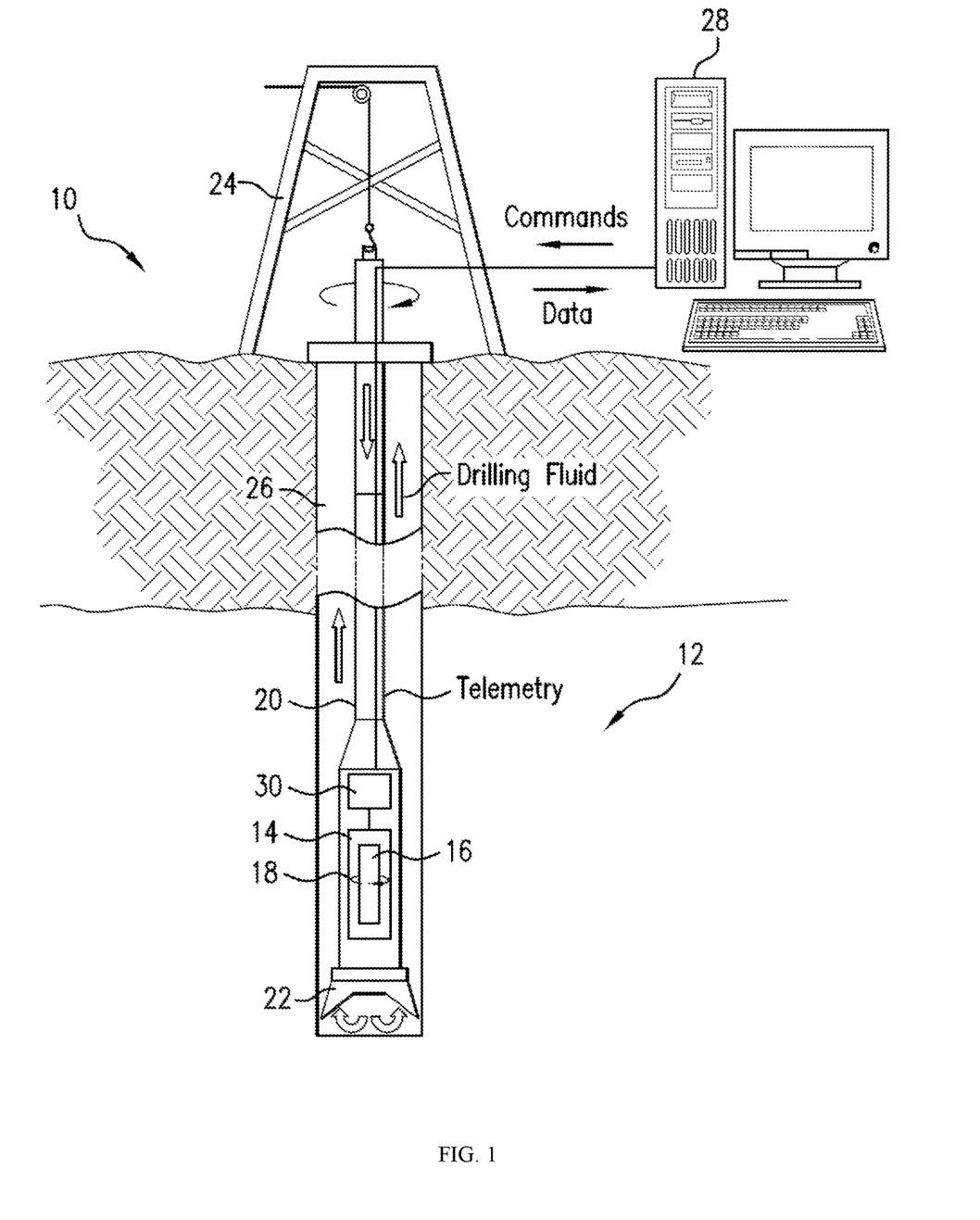
FIG. 1 depicts an embodiment of a formation measurement system that includes a nuclear magnetic resonance (NMR) measurement apparatus.

FIG. 1 illustrates an exemplary embodiment of a downhole measurement, data acquisition, and/or analysis system 10 that includes devices or systems for in-situ measurement of characteristics of an earth formation 12. The system 10 includes a magnetic resonance apparatus such as a NMR tool 14. An example of the magnetic resonance apparatus is a logging-while-drilling (LWD) magnetic resonance tool. The tool 14 is configured to generate magnetic resonance data for use in estimating characteristics of a formation, such as porosity, irreducible water saturation, permeability, hydrocarbon content, and fluid viscosity.

An exemplary tool 14 includes a static magnetic field source 16, such as a permanent magnet assembly, that magnetizes formation materials and a transmitter and/or receiver assembly 18 (e.g., an antenna or antenna assembly) that transmits radio frequency (RF) energy or pulsed energy that provides an oscillating magnetic field in the formation, and detects NMR signals as voltages induced in the receiver. The transmitter assembly 18 may serve the receive function, or distinct receiving antennas may be used for that purpose. It can be appreciated that the tool 14 may include a variety of components and configurations as known in the art of nuclear magnetic resonance or magnetic resonance imaging.

The tool 14 may be configured as a component of various subterranean systems, such as wireline well logging and LWD systems. For example, the tool 14 can be incorporated within a drill string 20 including a drill bit 22 or other suitable carrier and deployed downhole, e.g., from a drilling rig 24 into a borehole 26 during a drilling operation. The tool 14 is not limited to the embodiments described herein, and may be deployed in a carrier with alternative conveyance methods. A "carrier" as described herein means any device, device component, combination of devices, media and/or member that may be used to convey, house, support or otherwise facilitate the use of another device, device component, combination of devices, media, and/or member. Exemplary non-limiting carriers include drill strings of the coiled tube type, of the jointed pipe type, and any combination or portion thereof. Other carrier examples include casing pipes, wirelines, wireline sondes, slickline sondes, drop shots, downhole subs, bottom-hole assemblies, and drill strings.

In one embodiment, the tool 14 and/or other downhole components are equipped with transmission equipment to communicate ultimately to a surface processing unit 28. Such transmission equipment may take any desired form, and different transmission media and methods may be used, such as wired, fiber optic, and/or wireless transmission methods. Additional processing units may be deployed with the carrier. For example, a downhole electronics unit 30 includes various electronic components to facilitate receiving signals and collect data, transmitting data and commands, and/or processing data downhole. The surface processing unit 28, electronics 30, the tool 14, and/or other components of the system 10 include devices as necessary to provide for storing and/or processing data collected from the tool 14 and other components of the system 10. Exemplary devices include, without limitation, at least one processor, storage, memory, input devices, output devices, and the like.

Magnetic resonance measurements are performed by the NMR tool, which generates a static inhomogeneous magnetic field ($B_0$) in a volume within the formation (a volume of interest) using one or more magnets (e.g., the magnetic field source 16). An oscillating (e.g., RF) magnetic field ($B_1$), which is at least substantially perpendicular to the static magnetic field, is generated in the volume of interest. The volume of interest may be circular or toroidal around the borehole, and/or focused or directed toward a specific angular region (i.e., side-looking).

The surface processing unit 28, electronics 30 and/or other suitable processing device includes a processor configured to generate electrical pulses and transmit the pulses to the transmitter assembly, which in turn generates pulses of electromagnetic energy that induce the oscillating field $B_1$ in the volume of interest. Such a processing device may be referred generally as a pulse generator, which includes a microcontroller or other processor that is capable of transmitting a pulse sequence. The pulse sequence can be programmed or set based on parameters such as pulse duration, time intervals between pulses and time between successive pulse sequences (wait time).

When exposed to the magnetic field $B_0$, the spin axes of hydrogen nuclei in the formation precess around the direction of the $B_0$ field with the Larmor frequency, which is proportional to the strength of the magnetic field $B_0$. The direction of orientation of the field $B_0$ in the formation volume of interest is referred to as the longitudinal direction or z-direction.

Over time, the spin axes align themselves at distinct angles along the $B_0$ field and create a net magnetization (i.e., polarization), which will build up with the time constant $T_1$. $T_1$ of a fluid in a porous rock can be expressed as:

$$\frac{1}{T_1} = \frac{1}{T_{1B}} + \frac{1}{T_{1S}} \quad (1)$$

$T_{1B}$ is the $T_1$ relaxation time of the bulk fluid and is inversely proportional to the viscosity, e.g., $T_{1B}$ of very heavy oil is very short. $T_{1S}$ is the surface relaxation and is dependent on the pore size, e.g., $T_{1S}$ is very short (on the order of ms or less than 1 ms) for clay-bound water.

The longitudinal magnetization cannot be measured directly, but it can be manipulated by the $B_1$ field. The $B_1$ field will interact only with those spins at resonance condition (where the $B_1$ field oscillating frequency is equal to or substantially equal to the Larmor frequency), i.e., in an inhomogeneous $B_0$ field, the $B_1$ frequency band defines the sensed volume. For an NMR logging tool, the sensed volume is selected to be fully in the formation.

When the $B_1$ field is turned on, the magnetization will be rotated around the $B_1$ field by an angle proportional to the length of the pulse and to the strength of the $B_1$ field. Ideally, the $B_1$ field is oriented perpendicular to the $B_0$ field in the volume of interest, e.g., in the x-y plane orthogonal to the longitudinal or z-axis, where the z-axis points along $B_0$ in the volume of interest.

While the hydrogen nuclei realign their spin axes as a result of the action of the $B_1$ field, they do so at different rates because of inhomogeneities in the $B_1$ field. Upon termination of the $B_1$ field the nuclear magnetization precesses freely around the $B_0$ field. Because of inhomogeneity of the $B_0$ field, resulting in a spread of Larmor frequencies, the bulk magnetization rapidly loses phase coherence (dephases), which causes a rapid decrease in the voltage induced in a receiver. This decrease is referred to as the free induction decay (FID).

$T_2$ is a time constant known as the transversal relaxation. It describes the loss of magnetization in the plane orthogonal to the $B_0$ field. $T_2$ decay can be written as:

$$\frac{1}{T_2} = \frac{1}{T_{2B}} + \frac{1}{T_{2S}} + \frac{1}{T_{2D}} \quad (2)$$

$T_{2D}$ is the $T_2$ relaxation time due to diffusion in the magnetic field gradient. $T_{2D}$ depends on the inter-echo time (TE), on the molecular diffusion coefficient, D, and on the $B_0$ field gradient (G). For a low-magnetic-field-gradient tool, $T_{2D}$ is typically considerably larger than $T_2$ and the recorded $T_2$ distribution is usually quite similar to the $T_1$ distribution. The $T_1/T_2$ ratio is usually between 1 and 3. However, in the presence of iron minerals the internal field gradients increase significantly, which in turn enhances the $T_2$ diffusion decay, i.e. $T_{2D}$ decreases, and $T_2$ gets smaller.

The B1 field is typically applied as a series of short duration pulses, which may be rectangular or other shaped pulses. In an embodiment of a pulse sequence, the first pulse is a "tipping pulse", which acts to align the nuclear magnetization in the formation in a direction perpendicular to the static field $B_0$, e.g., rotate the magnetization from the z-direction into the x-y plane. After the tipping pulse, the nuclear magnetic moment of the nuclei gradually return or "relax" to their alignment with the static field.

At a selected time after the beginning of the FID from the tipping pulse, a first "refocusing pulse" is applied, which has a duration and amplitude selected to at least partly reverse the magnetizations of microscopic volume elements. In consequence the coherent macroscopic magnetization that was lost after the tipping pulse rephases now after the refocus pulse, resulting in a so-called spin echo that induces a measurable voltage in the receiving antenna. Hence, the tipping pulse, followed by a refocus pulse, generates a first "direct echo", the maximum amplitude of which is proportional to the porosity in the formation.

In an inhomogeneous $B_0$ field, a refocus pulse cannot keep all of the original magnetization in the x-y plane and some of it is rotated into the z-direction. This magnetization stored in the z-direction will not contribute to the first echo. However, a second refocus pulse will recall some of the magnetization from the z-direction into the x-y plane and will create a first "stimulated echo." Simultaneously, the second refocus pulse will also refocus the de-phased first direct echo and a second direct echo will be created.

The refocus pulses restore only the transversal magnetization that gets lost due to the inhomogeneity of the $B_0$ field. The loss of magnetization due to relaxation processes cannot be restored and will happen with the time constant $T_2$ (with a contribution of $T_1$ due to the stimulated echo contributions).

The timing of the pulses is typically selected in such a way that the time when the second direct echo appears corresponds to the time when the first stimulated echo appears. The sum of the two echoes is usually referred to as an NMR echo or simply as an echo. Further refocus pulses will also create direct and non-direct echoes which occur simultaneously, resulting in overlapping echoes that are referred to below as contaminated echoes or composite echoes. A "non-direct echo" is an echo formed by magnetization which is not always in the x-y plane. The stimulated echo is usually a large-amplitude non-direct echo. Some other non-direct echoes and non-stimulated echoes have small amplitudes. An example of one such pulse sequence with composite echoes and often used in NMR is the well-known Carr-Purcell-Meiboom-Gill (CPMG) pulse sequence, which has a constant time $2*\tau=T_E$ between the refocus pulses, where "$\tau$" is the time between the tipping pulse and the first refocusing pulse. The advantage of a CPMG-like sequence is its simplicity (equal spacing between refocus pulses and echoes), the constant echo spacing ($T_E$) and relatively high echo signals.

The CPMG pulse sequence parameters include wait time ($T_W$), echo spacing ($T_E$), the number of echoes ($N_E$), and the number of sequence repetitions. Parameters may be selected based on considerations such as anticipated formation properties and anticipated fluid types and properties. $T_W$ (the time elapsed between successive pulse sequences) can be selected to measure different formation types and regions expected to have different $T_1$ ranges. For example, longer wait times ($T_W$) usually in connection with a larger number of echoes, are useful for movable or non-wetting fluids, and shorter wait times ($T_W$) are useful for shaly formations. Note that, for a CPMG pulse sequence, the inter-pulse time interval is the same as the inter-echo time interval, TE.

In contrast to all other echoes, the first echo of a CPMG pulse sequence is a "clean" direct echo and has no contribution from a non-direct echo. "Clean" in this context means that the direct echo is affected by $T_2$ relaxation only, i.e. not affected by $T_1$ relaxation. The echoes following the first echo are contaminated or composite echoes, i.e., their amplitudes are sums of amplitudes of direct echoes and non-direct echoes.

The first echo from a CPMG pulse sequence is a clean direct echo. All the other echoes from a CPMG pulse sequence are composite echoes. If $T_1$ equals $T_2$, then the amplitudes of the echo train decay exponentially except for the first few echoes (typically the first two or three echoes). The amplitude of the first echo is significantly below the exponential decay, while the amplitudes of the second and third echo are only slightly different from the exponential decay. We call this effect the "first-order stimulated-echo effect" (FOSTE). The occurrence of the effect is not tool specific (as opposed to the size of the effect, which can vary, resulting in a specific first-order stimulated echo correction factor of a particular NMR tool) but is present for all NMR tools with inhomogeneous magnetic fields, i.e. for all NMR logging tools.

First-order stimulated echo corrections may be applied to the echo train to account for contributions of stimulated echoes. For example, a multiplicative correction value (a STE correction value) may be applied to the amplitude of the first direct echo to increase its amplitude to the level of the subsequent echoes that have stimulated echo contributions. Individual correction values or factors "STEx" may be applied to echoes in the echo train, where "x" is the echo number (e.g., the first direct echo is labeled echo 1, and subsequent composite echoes would be labeled echo 2, echo 3 . . . ).

STE correction values may be determined during the calibration process by using a sample with known porosity (e.g., 100 p.u.) and long T2 value. Data has indicated that, as expected the first echo shows lower amplitude, but also that the amplitudes of the second and third echo are also slightly affected.

If $T_1$ is equal to or substantially equal to $T_2$, numerical simulations and experiments have shown that, excepting the first three echoes, the echo-train amplitude will decay with the $T_2$ time constant. In this case, the first-order stimulated echo correction factors STE1 to STE3 may be applied to the first three echoes to adjust their amplitudes to fit the $T_2$ decay rate.

Such first-order STE correction factors for logging data do not take into account that the magnetization that creates the stimulated echo has a mixed relaxation, i.e., during at least one inter-pulse time interval the relaxation is not in the x-y plane (with the $T_2$ time constant) but in the z direction (with the $T_1$ time constant).

NMR methods using prior art pulses sequences such as CPMG sequences (LWD or wireline) can deliver an inaccurate micro-porosity (porosity characterized by very short T2 values, such as clay-bound water (CBW), very heavy oil, or porosity from very small pores in a carbonate rock). Such inaccuracies can deliver potentially significant porosity overcall if the first echo, which is frequently affected by apparatus artifacts (ringing), is not processed. The cause for the porosity overcall is the stimulated echo which does not relax throughout with the transversal relaxation time, $T_2$, but also relaxes for part of the time with the longitudinal relaxation time $T_1$. If $T_1$ is longer than $T_2$, the combined relaxations, which contribute in variable proportions to the echoes, result in non-exponential echo decay. Typically, the subsequent $T_2$ inversion leads to porosity undercall if the first echo is processed, or to porosity overcall if the first echo is excluded from the processing. This effect is referred to as the "second-order stimulated-echo effect" (SOSTE).

Embodiments of NMR systems and methods described herein utilize a pulse sequence, referred to herein as a "direct-echo pulse sequence", which is configured to separate the direct echo from the non-direct echo(es) following a refocusing pulse. In contrast to the CMPG pulse sequence, the direct-echo pulse sequence may have a variable time between refocus pulses. This direct-echo pulse sequence may be used to directly compute accurate NMR porosity, or as a means to correct NMR data acquired and processed with other methods and/or pulse sequences.

Use of the direct-echo pulse sequence is an effective technique for addressing the second-order stimulated echo effect, as it fully or partially separates non-direct echoes from direct echoes, resulting in clean or partially clean direct echoes. Porosity derived from this sequence will thus not suffer (at least substantially) from the second-order stimulated echo effect.

The direct-echo pulse sequence might have a variable time between refocus pulses, so that the coincidence of direct and non-direct echoes can be avoided. The direct-echo pulse sequence creates at least a second "clean" direct echo in addition to the first direct echo (which was generated by the first pulse and is "clean" because it is not affected by previous T1 relaxation). Thus, in contrast to pulse sequences such as the CPMG sequence, the second refocusing pulse in the direct-echo pulse sequence generates a direct echo that is separated from the stimulated echo.

Figure 2:
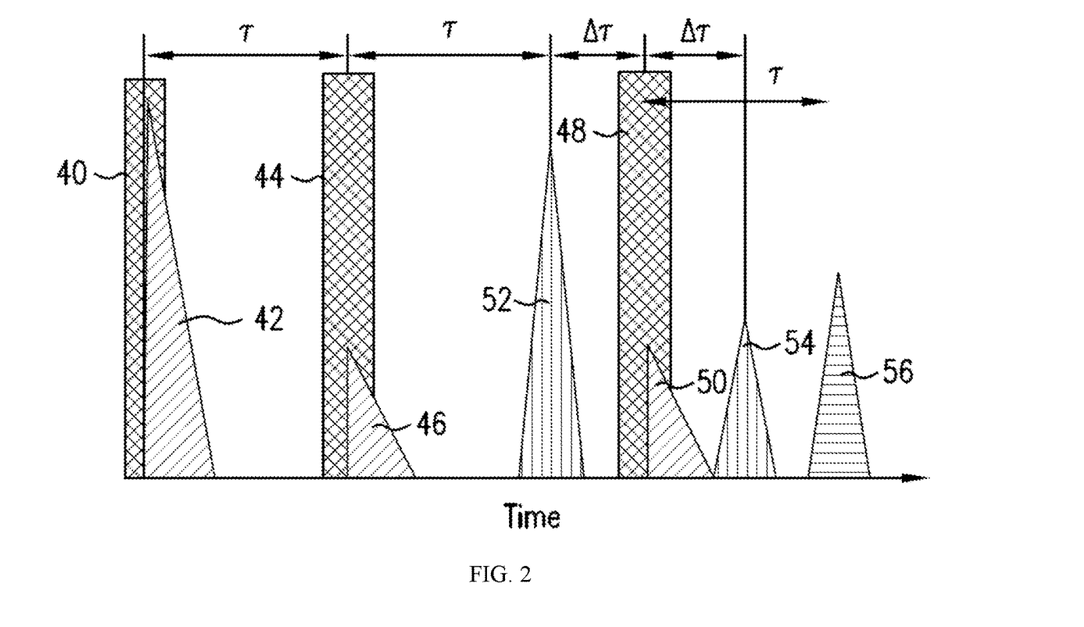
FIG. 2 depicts an embodiment of a direct-echo pulse sequence for use in transmitting an electromagnetic signal into a formation, the signal inducing an oscillating magnetic field in the formation.
Figure 3:
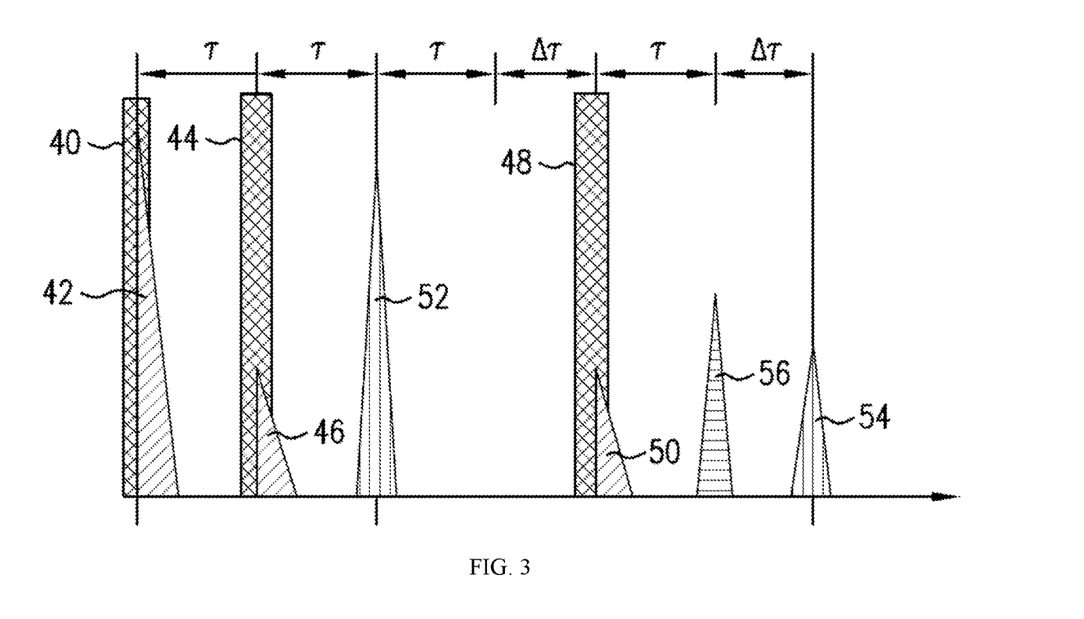
FIG. 3 depicts another embodiment of a direct-echo pulse sequence for use in transmitting an electromagnetic signal into a formation.

FIGS. 2 and 3 illustrate embodiments of a direct-echo pulse sequence. The pulse sequence begins with a tipping pulse, and is followed by a plurality of refocusing pulses applied at selected times or after selected time intervals. A tipping pulse 40 is applied at an initial time (also referred to as time zero), which includes a first FID 42. At a selected time "$\tau$" after the tipping pulse 40 (a first time interval), a first refocusing pulse 44 is applied, which induces another FID decay 46. A second refocusing pulse 48 produces yet another FID decay 50. In addition, the first refocusing pulse 44 induces a first direct echo 52 (which is clean) at time $2\tau$, and the second refocusing pulse induces a second direct echo 54 and a separate stimulated echo 56. The second direct echo 54 is clean if $\Delta t$ is chosen such that echo 54 does not overlap with the stimulated echo 56. "$\Delta t$" is further discussed below.

The second refocusing pulse 48 is applied at a second time interval after the first refocusing pulse. The second time interval is not twice the first time interval between the tipping pulse 40 and the first refocusing pulse 44. This is in contrast to pulse sequences such as the CPMG sequence, where the time interval between refocus pulses is $2*\tau$, where $\tau$ is the time interval between the tipping pulse 40 and the first refocus pulse 44. It is noted that the time or temporal location of a pulse is identified in relation to the action center of the pulse. Thus, "between" two pulses means "between the action centers" of two pulses.

The second time interval is equal to a multiple of $\tau$ increased or reduced by a variable time value "$\Delta t$" (e.g., $2*\tau+\Delta t$ or $2*\tau-\Delta t$), which is selected to produce non-overlapping or separate non-direct echoes and direct echoes. $\Delta t$ may be determined numerically based on selected rules, or determined experimentally or by NMR simulation. For example, $\Delta t$ is selected to lead to the smallest possible value of the time of the direct echo(es) in such a way that the amplitude of the direct echo(es) is usable without additional corrections due to the interference with a non-direct echo. The interference with a non-direct echo might be either due to overlapping with a large-amplitude stimulated echo or due to superposition with a non-direct echo of low amplitude. A direct echo which is not a clean direct echo, but which can be used in further processing is a "slightly contaminated direct echo".

In one embodiment, shown in FIG. 2, the second time interval is equal to the sum of $\tau$ and $\Delta t$, where $\Delta t$ is equal to the time interval between the direct echo 52 and the second refocusing pulse 48 and equal to the time interval between the second refocusing pulse 48 and the second direct echo 54. An exemplary value for $\tau$ is about 0.4 ms and an exemplary value for $\Delta t$ is 0.2 ms.

In another embodiment, shown in FIG. 3, the second time interval is equal to the sum of $2*\tau$ and $\Delta t$, where the time interval between the direct echo 52 and the second refocusing pulse 48 is equal to $\tau+\Delta t$, and the time interval between the second refocusing pulse 48 and the second direct echo 54 is also equal to $\tau+\Delta t$. An exemplary value for $\tau$ is about 0.2 ms and an exemplary value for $\Delta t$ is also 0.2 ms.

The pulse sequence of FIG. 2 may be preferable because the direct echoes are closer to time zero. However, direct echo 54 of this sequence might be affected by ringing, in which case the sequence of FIG. 3 may be preferable because, with respect to the direct echo 54, the sequence is more robust against ringing.

The direct-echo pulse sequence can have more than three pulses, and the multiple of $\tau$ may be more than one or two. For example, to generate a third clean echo, the time interval between the second refocusing pulse 48 and a third successive refocusing pulse is selected so that the distance between the second refocusing pulse 48 and the third refocusing pulse produces a third direct echo that is separate from the non-direct echoes induced by the third refocusing pulse. In some cases, this third time interval can be quite large. For example, for the sequence of FIG. 3, the time interval between the pulse 48 and the next refocusing pulse will be $5*\tau+2*\Delta t$.

Figure 5:
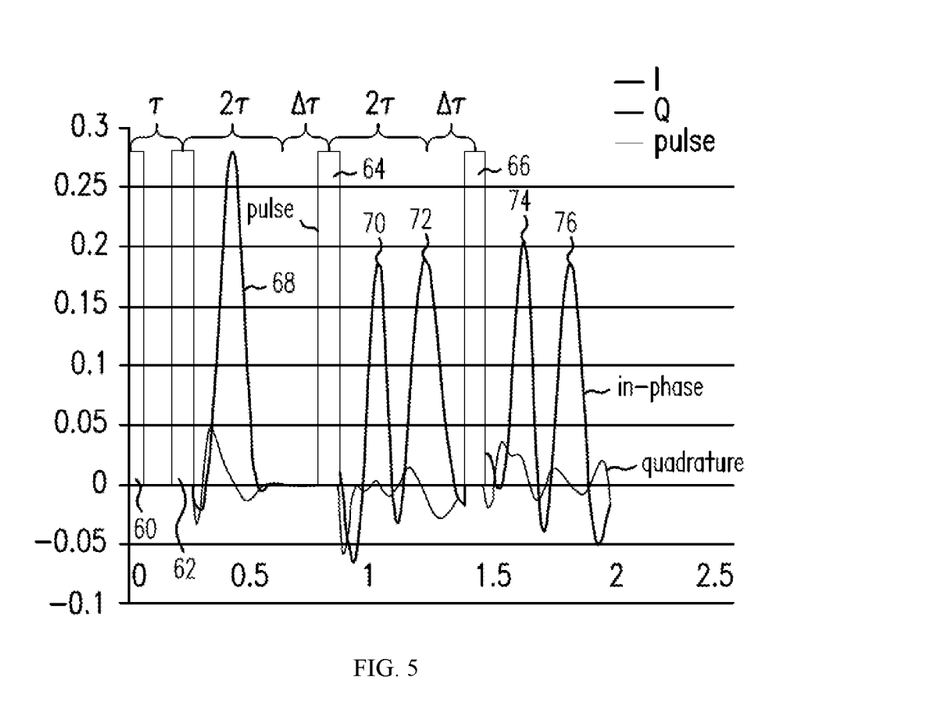
FIG. 5 depicts a simulation of another embodiment of a direct-echo pulse sequence.

To balance considerations of accuracy and the desire to have more clean echoes at the earliest possible times after the tipping pulse (for a proper characterization of clay-bond-water, for example), the time $5*\tau+2*\Delta t$ between the second and third refocus pulses in an extended FIG. 3 can be reduced so that the non-direct echoes and direct echoes are not completely separate, i.e., have some overlap. For example, the timing of the third refocusing pulse can be selected in such a way, to create a direct echo which is only slightly contaminated by a non-direct echo, i.e., the non-direct echo has only a small contribution to that echo (an example of this is shown in FIG. 5).

In one embodiment, a correction referred to as a Direct Echo (DE) correction is applied to the direct echoes resulting from the direct-echo pulse sequence to correct for the different amplitudes of the (clean) direct echoes. The corrected direct echoes may then be used to estimate porosity and/or T2 of the formation.

The DE correction is performed to correct the amplitude of all direct echoes (clean or contaminated) except the first one. In some cases, DE correction is similar to STE correction discussed above. For example, the amplitude of one or more direct echoes is multiplied by a DE correction value.

The DE correction values are determined during the calibration process in a similar way as the STE correction values. For example, values for the DE correction are determined by acquiring direct echo amplitudes with a calibration sample for which T2 (and T1) is much longer than the total acquisition time of the direct-echo pulse sequence. The amplitudes of the direct echoes are ADEx, whereby "x" is the number of the direct echo. The DE correction value for the direct echo number "x" is DEx=ADE1/ADEx.

Inversion of an echo-train recorded with the direct-echo pulse sequence will lead to a $T_2$ distribution which is not affected (or only slightly affected) by the second-order stimulated echo effect. The direct-echo pulse sequence can be used as a standalone pulse sequence. In this case it will provide porosities which are not affected (or only slightly affected) by the second-order stimulated echo effect. In some embodiments, the direct-echo pulse sequence is used in conjunction with one or more CPMG sequences or other sequences. In such embodiments, data from the direct-echo pulse sequence provides a means to apply a second-order stimulated echo correction on the CPMG or other pulse sequence data.

For example, a direct-echo pulse sequence can be recorded with the same wait time as a relatively short CPMG pulse sequence, e.g., a wait time corresponding to expected $T_1$ values associated with clay-bound water. Using the resulting data sets together allows for estimation of the porosity error, e.g., porosity overcall. The porosity overcall can be subtracted from the $T_2$ distribution of the longer sequence based only on CPMG data. An alternative way is the multiplication of the porosity estimated using a CPMG sequence with a correction factor. This correction factor might depend on $T_2$ and/or $T_1$.

Figure 4:
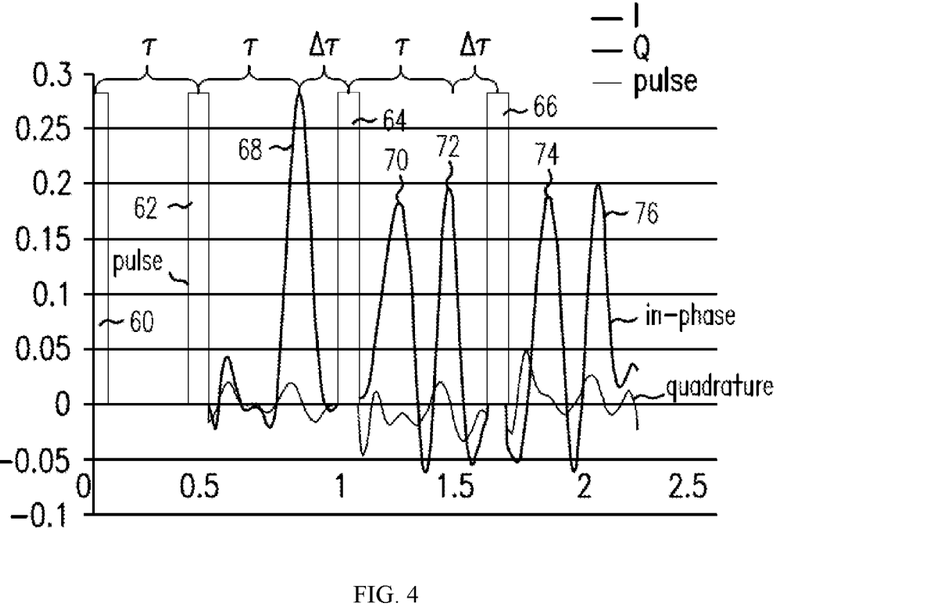
FIG. 4 depicts a simulation of an embodiment of a direct-echo pulse sequence.

FIGS. 4 and 5 show simulations of embodiments of the direct-echo pulse sequence, which illustrate pulse sequences that utilize both clean direct echoes and slightly contaminated direct echoes. NMR signals are RF signals and, after down conversion into base band, split into in-phase and quadrature channels, both channels being shown in FIGS. 4 and 5 after phase correction. FIG. 4 shows a numerical simulation of a pulse sequence that includes a tipping pulse 60 at time zero, a first refocusing pulse 62 at time $\tau$, a second refocusing pulse 64 at time $2*\tau+\Delta t$, and a third refocusing pulse 66 at time $3*\tau+2*\Delta t$. In this embodiment, $\tau$=about 0.4 ms and $\Delta t$=about 0.2 ms. First and second echoes 68 and 70 are clean direct echoes. Echo 72 is the first stimulated echo, echo 74 is a composite echo having a relatively large part of the stimulated echo (a contaminated echo), and echo 76 is a direct echo of the clean direct echo 70, but having also a relatively small contribution of a non-direct echo. Hence, echo 76 is a slightly contaminated direct echo.

FIG. 5 shows a similar pulse sequence using a time interval of $2*\tau+\Delta t$ between first and second refocusing pulses, where $\tau$=about 0.2 ms and $\Delta t$=about 0.2 ms. In this example, echoes 68 and 72 are clean direct echoes and echo 74 is a slightly contaminated direct echo.

Figure 6:
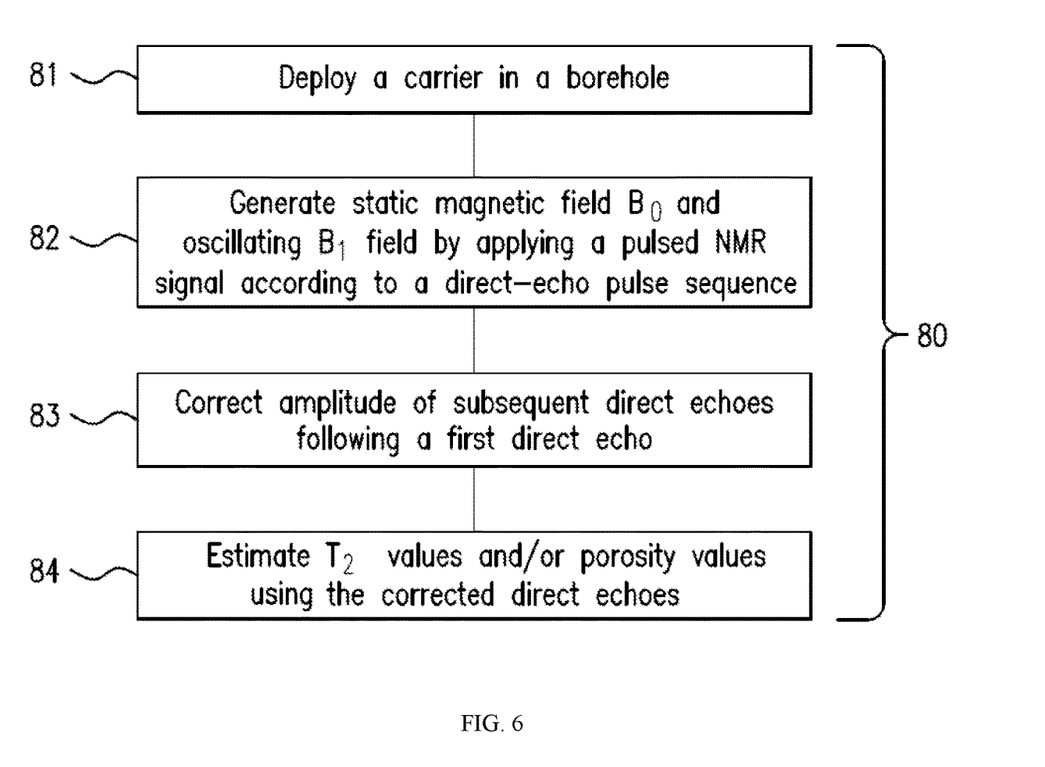
FIG. 6 is a flow chart that depicts an embodiment of a NMR measurement method that includes transmitting an electromagnetic signal with a direct-echo pulse sequence.

FIG. 6 illustrates a method 80 for performing an NMR measurement operation that includes using a direct-echo pulse sequence, as a stand alone or in conjunction with a CPMG or other conventional pulse sequence. The method may be performed in conjunction with the system 10, but is not limited thereto. The method 80 includes one or more of stages 81-84 described herein, at least portions of which may be performed by a processor (e.g., the surface processing unit 28). In one embodiment, the method 80 includes the execution of all of stages 81-84 in the order described. However, certain stages 81-84 may be omitted, stages may be added, or the order of the stages changed.

In the first stage 81, an NMR or other magnetic resonance measurement tool is deployed into a borehole. In one embodiment, the tool (e.g., the tool 14) is deployed as part of a wireline operation, or during drilling as part of a LWD operation.

In the second stage 82, a static magnetic field $B_0$ is generated in a volume of interest in the formation, and a pulsed signal is transmitted from at least one transmitting antenna according to the direct-echo pulse sequence, which in turn generates an oscillating magnetic field $B_1$ in the volume of interest. At least one receiving antenna detects NMR signals from the volume in response to the interaction between the nuclear spins of interest and the static and oscillating magnetic fields, and generates raw NMR data. The raw NMR data includes spin echo trains that may be measured at a plurality of depths. The echo trains include direct and non-direct echoes as discussed above.

Detecting the raw NMR data may include detecting both direct and non-direct echoes, or detecting the direct echoes (clean and contaminated) and either not detecting the non-direct echoes or discarding the non-direct echoes. For example, if only $T_2$ information is desired, only the clean and slightly contaminated direct echoes need be considered. If information regarding $T_1$ is desired, the direct echoes are used to determine $T_2$, and further information regarding $T_1$ may be acquired using both direct and stimulated echoes.

In the third stage 83, in one embodiment, before using the amplitude of the direct echoes to estimate the porosity and/or T2, a DE correction is performed to correct the amplitude of all direct echoes except the first one. In some cases, DE correction is similar to STE correction discussed above.

At least two clean direct echoes are acquired and identified, and the DE correction is applied to the clean direct echoes. The DE correction can be extended to include also slightly contaminated direct echoes.

For example, a sequence such as that shown in FIG. 4 is selected, and direct echoes are detected. In this example, the direct echoes are echo 68 (the first clean direct echo), echo 70 (the second clean direct echo), and echo 76 (the third direct echo, which is slightly contaminated). DEx values based on data using known media (e.g., water samples) are applied to the direct echoes to correct the direct echoes.

In the fourth stage 84, a T2 or porosity value is estimated using the amplitude of at least two direct echoes from the direct-echo pulse sequence and the DE correction value. For example, the DE correction is performed and a T2 inversion is applied to derive T2 and/or porosity values. The DE correction and T2 inversion may be performed consecutively or simultaneously (i.e., in a single processing step).

Alternatively, instead of T2 inversion, a fit of an exponential function or a sum of at least two exponential functions to the at least two DE-corrected direct echoes may be employed to estimate T2 or porosity.

Figure 7:
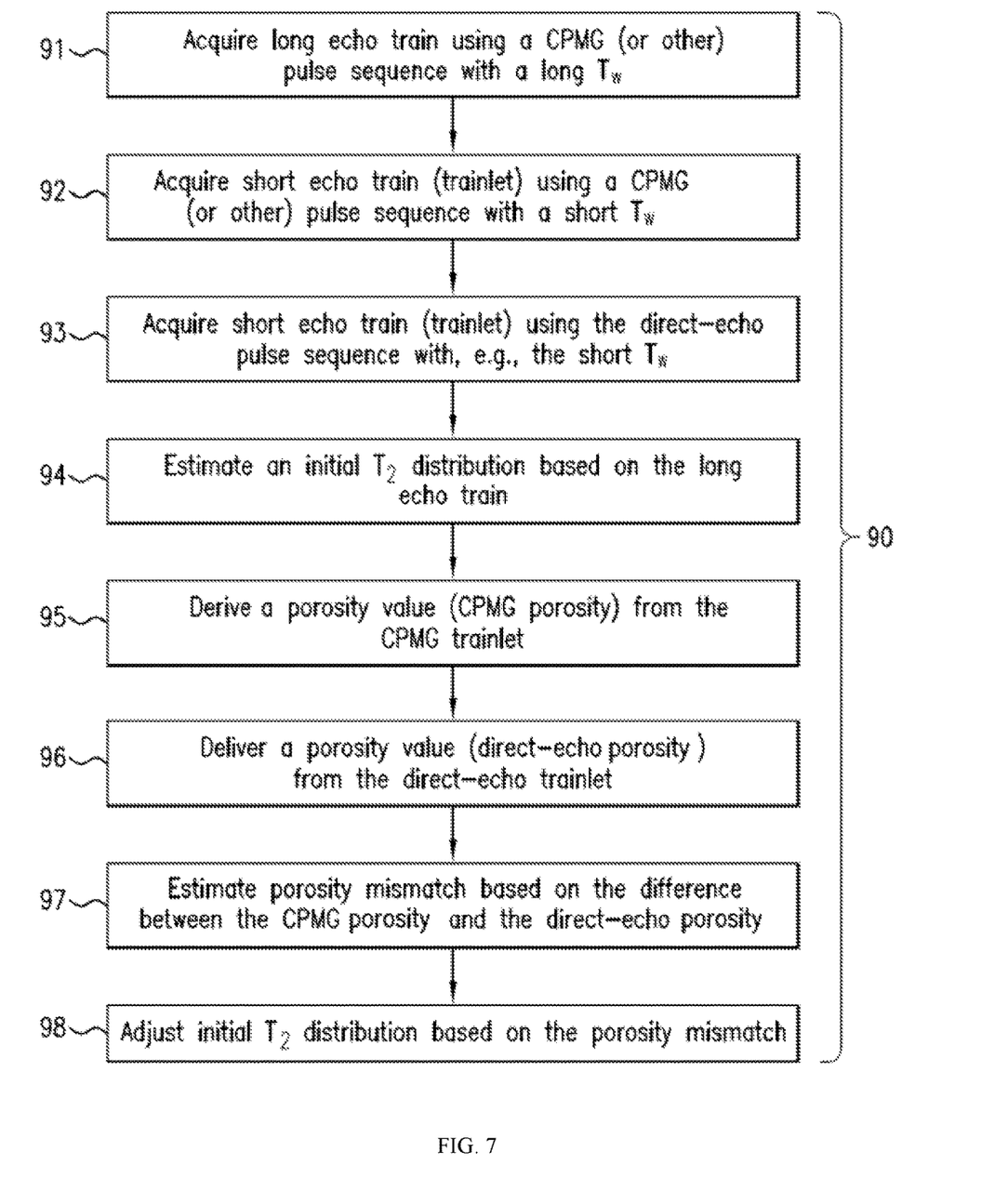
FIG. 7 is a flow chart that depicts an embodiment of a NMR measurement method that includes correcting NMR signals and/or porosity values using porosity data derived using a direct-echo pulse sequence.

FIG. 7 illustrates a method 90 for performing an NMR operation, which includes acquiring NMR signals using the direct-echo pulse sequence in conjunction with a CPMG or other type of pulse sequence. The method may be performed in conjunction with the system 10, but is not limited thereto. The method 90 includes one or more of stages 91-98 described herein, at least portions of which may be performed by a processor (e.g., the surface processing unit 28). In one embodiment, the method 90 includes the execution of all of stages 91-98 in the order described. However, certain stages 91-98 may be omitted, stages may be added, or the order of the stages changed.

In the first stage 91, an NMR or other magnetic resonance measurement tool is deployed into a borehole, and NMR data is acquired by generating a static magnetic field $B_0$ in the surrounding formation volume, and transmitting a pulsed signal using a pulse sequence such as a CPMG pulse sequence with a wait time ($T_W$) sufficient to polarize some or all (or nearly all) of the borehole fluids. This wait time is referred to as a long wait time (long $T_W$), and the echo train acquired using the long $T_W$, which can have a large number (e.g., on the order of many hundreds to few thousands) of echoes, is referred to as a "long echo-train". Optionally, first-order STE correction is applied to the long echo train.

In the second stage 92, a second pulse sequence such as a CPMG pulse sequence is applied to the formation with a $T_W$ (referred to as a short $T_W$) that is shorter than that associated with the "long echo-train". In one embodiment, the short $T_W$ is selected so that the time is sufficient to polarize only clay bound water or another selected fluid or formation material. The acquired echo-train is referred to as a "CPMG short echo train" or a "CPMG trainlet", which typically has fewer echoes than the long echo train. Optionally, first-order STE correction is applied to the trainlet. Although the CPMG trainlet is derived using a CPMG sequence, other suitable sequences may be used instead. Thus, terminology used herein that includes "CPMG" is not intended to limit any embodiments to using only CPMG sequences.

In the third stage 93, an echo train is acquired using a direct-echo pulse sequence as discussed above. This echo train may be referred to as a "direct-echo trainlet." The $T_W$ used for this pulse sequence may be of any selected length. In one embodiment, the direct-echo pulse sequence is applied with a wait time that is substantially the same or similar to the short $T_W$ used for the second pulse sequence, although the $T_W$ used for the direct-echo pulse sequence may be different than that used for the second pulse sequence. DE correction may be applied to the direct-echo trainlet.

In the fourth stage 94, the long echo train is inverted to obtain an initial $T_2$ distribution. In one embodiment, the first echo in the long echo train is excluded from the inversion. The initial T2 distribution is used to create a "pseudo echo trainlet", by applying the initial T2 distribution over the short TW.

In the fifth stage 95, a porosity value is derived from the CPMG trainlet, which is referred to as the "CPMG trainlet porosity". In one embodiment, the pseudo echo trainlet is subtracted from the CPMG trainlet, and the result is inverted to estimate the CPMG trainlet porosity. In one embodiment, the first echo is excluded from the inversion.

In the sixth stage 96, a porosity value is derived from the direct-echo trainlet, which is referred to as the "direct-echo trainlet porosity". In one embodiment, the pseudo echo trainlet is subtracted from the direct-echo trainlet, and the result is inverted to estimate the direct-echo trainlet porosity.

In the seventh stage 97, the difference between the CMPG trainlet porosity and the direct-echo trainlet porosity is a porosity mismatch. Typically, the CPMG trainlet porosity is larger than the direct-echo trainlet porosity, and the porosity mismatch is a porosity overcall.

In the eighth stage 98, the initial T2 distribution is adjusted as a function of the difference or discrepancy between the CPMG trainlet and the direct-echo trainlet. For example, the adjustment might be the subtraction (or correction) of the porosity overcall from the porosity distribution. A simple implementation would be to correct only the CBW porosity.

In one embodiment, the correction is not equally distributed over all porosity bins. Porosity bins with short T2 values will be proportionally more affected than the porosity bins with large T2.

Although the method 90 is described as using inversion of a CPMG echo train or trainlet without using the first echo, the method is not so limited. For example, the method 90 may include an inversion where the first echo is used in the inversion. The effect of the first echo on the final result may be diminished, for example, by reducing or altering the weight of first echo amplitude using a weighting factor.

Embodiment 1

A nuclear magnetic resonance (NMR) apparatus for estimating properties of an earth formation downhole, the apparatus comprising: a carrier configured to be deployed in a borehole in the earth formation; a magnet assembly disposed in the carrier and configured to generate a static magnetic field in the formation; at least one transmitting assembly disposed in the carrier and configured to generate an oscillating magnetic field in a volume of interest within the formation; a pulse generator configured to apply a direct-echo pulse sequence to the at least one transmitting assembly, the direct-echo pulse sequence having a plurality of successive pulses, the plurality of successive pulses including a first pulse and a second pulse configured to generate a first direct NMR echo, and a third pulse, the third pulse selected to at least partially separate a stimulated NMR echo from a second direct NMR echo occurring after the third pulse; and at least one receiving assembly disposed in the carrier and configured to detect the first and second direct NMR echoes of an NMR echo train.

Embodiment 2

The apparatus of any prior embodiment, wherein the center of the first pulse and the center of the second pulse are separated by a first time interval $\tau$, and the center of the second pulse and the center of the third pulse are separated by a second time interval that is not substantially equal to $2\tau$.

Embodiment 3

The apparatus of any prior embodiment, wherein the second time interval is substantially equal to a sum of $\tau$ and a time value $\Delta t$, a sum of a multiple of $\tau$ and the time value $\Delta t$, or a difference between a multiple of $\tau$ and the time value $\Delta t$, the time value $\Delta t$ being substantially equal to half of $\tau$.

Embodiment 4

The apparatus of any prior embodiment, further comprising a processor configured to perform a correction of at least one of the first and second direct NMR echoes.

Embodiment 5

The apparatus of any prior embodiment, wherein the correction is performed by applying the direct-echo pulse sequence to a calibration sample and using a plurality of direct echoes acquired from the calibration sample, or wherein the correction is performed based on an NMR simulation.

Embodiment 6

The apparatus of any prior embodiment, further comprising a processor configured to estimate at least one of a porosity value and a $T_2$ value of the formation based on the NMR echo train.

Embodiment 7

The apparatus of any prior embodiment, further comprising a processor configured to acquire at least one separate NMR echo train and perform a correction of NMR data associated with the at least one separate NMR echo train, the correction based on the first and second direct NMR echoes.

Embodiment 8

The apparatus of any prior embodiment, wherein the at least one separate NMR echo train includes a first echo train acquired using a first CPMG-type sequence, the first CPMG-type sequence and the direct-echo pulse sequence having a wait time that is substantially the same.

Embodiment 9

The apparatus of any prior embodiment, wherein the correction is based on an inequality between a porosity derived from the first CPMG-type sequence and a porosity derived from the direct-echo sequence.

Embodiment 10

The apparatus of any prior embodiment, wherein the at least one separate NMR echo train includes a second echo train acquired using a second CPMG-type pulse sequence having a wait time that is longer than the wait time associated with the first CPMG-type sequence and the direct-echo pulse sequence, and the processor is configured to correct a $T_2$ distribution obtained from the second CPMG-type pulse sequence based on the inequality.

Embodiment 11

A method of estimating properties of an earth formation downhole, the method comprising: deploying a carrier into a borehole in the earth formation; generating a static magnetic field in a volume of interest within the formation by a magnet assembly disposed in the carrier; emitting pulses of an electromagnetic signal, by at least one transmitting assembly disposed in the carrier, into the volume of interest to generate an oscillating magnetic field, the pulses emitted as a direct-echo pulse sequence having a plurality of successive pulses, the plurality of successive pulses including a first pulse and a second pulse configured to generate a first direct NMR echo, and a third pulse, the third pulse selected to at least partially separate a stimulated NMR echo from a second direct NMR echo occurring after the third pulse; and estimating a property of the volume of interest by a processor based on amplitudes of at least the first and second direct echoes of an NMR echo train resulting from the pulse sequence.

Embodiment 12

The method of any prior embodiment, wherein the center of the first pulse and the center of the second pulse are separated by a first time interval $\tau$, and the center of the second pulse and the center of the third pulse are separated by a second time interval that is not substantially equal to $1\tau$.

Embodiment 13

The method of any prior embodiment, wherein the second time interval is substantially equal to a sum of $\tau$ and a time value $\Delta t$, a sum of a multiple of $\tau$ and the time value $\Delta t$, or a difference between a multiple of $\tau$ and the time value $\Delta t$, the time value $\Delta t$ being substantially equal to half of $\tau$.

Embodiment 14

The method of any prior embodiment, further comprising a processor configured to perform a correction of at least one of the first and second direct NMR echoes.

Embodiment 15

The method of any prior embodiment, wherein the correction is performed by applying the direct-echo pulse sequence to a calibration sample and using a plurality of direct echoes acquired from the calibration sample, or wherein the correction is performed based on an NMR simulation.

Embodiment 16

The method of any prior embodiment, further comprising a processor configured to estimate at least one of a porosity value and a $T_2$ value of the formation based on the NMR echo train.

Embodiment 17

The method of any prior embodiment, further comprising a processor configured to acquire at least one separate NMR echo train and perform a correction of NMR data associated with the at least one separate NMR echo train, the correction based on the first and second direct NMR echoes.

Embodiment 18

The method of any prior embodiment, wherein the at least one separate NMR echo train includes a first echo train acquired using a first CPMG-type sequence, the first CPMG-type sequence and the direct-echo pulse sequence having a wait time that is substantially the same.

Embodiment 19

The method of any prior embodiment, wherein the correction is based on an inequality between a porosity derived from the first CPMG-type sequence and a porosity derived from the direct-echo sequence.

Embodiment 20

The method of any prior embodiment, wherein the at least one separate NMR echo train includes a second echo train acquired using a second CPMG-type pulse sequence having a wait time that is longer than the wait time associated with the first CPMG-type sequence and the direct-echo pulse sequence, and the processor is configured to correct a $T_2$ distribution obtained from the second CPMG-type pulse sequence based on the inequality.

In connection with the teachings herein, various analyses and/or analytical components may be used, including digital and/or analog subsystems. The system may have components such as a processor, storage media, memory, input, output, communications link (wired, wireless, pulsed mud, optical or other), user interfaces, software programs, signal processors and other such components (such as resistors, capacitors, inductors, etc.) to provide for operation and analyses of the apparatus and methods disclosed herein in any of several manners well-appreciated in the art. It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user, or other such personnel, in addition to the functions described in this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention.

What is claimed is:

1. A nuclear magnetic resonance (NMR) apparatus for estimating properties of an earth formation downhole, the apparatus comprising:
    a carrier configured to be deployed in a borehole in the earth formation;
    a magnet assembly disposed in the carrier and configured to generate a static magnetic field in the formation;
    at least one transmitting assembly disposed in the carrier and configured to generate an oscillating magnetic field in a volume of interest within the formation;
    a pulse generator configured to apply a direct-echo pulse sequence to the at least one transmitting assembly, the direct-echo pulse sequence having a plurality of successive pulses, the plurality of successive pulses including a first pulse and a second pulse configured to generate a first clean direct NMR echo, and a third pulse, the third pulse selected to at least partially separate a stimulated NMR echo from a second clean direct NMR echo occurring after the third pulse; and
    at least one receiving assembly disposed in the carrier and configured to detect the first and second clean direct NMR echoes of an NMR echo train; and
    a processor configured to acquire at least one separate NMR echo train and perform a correction of NMR data associated with the at least one separate NMR echo train, the correction based on the first and second clean direct NMR echoes.

2. The apparatus of claim 1, wherein the center of the first pulse and the center of the second pulse are separated by a first time interval $\tau$, and the center of the second pulse and the center of the third pulse are separated by a second time interval, wherein the second time interval is not substantially equal to $2\tau$.

3. The apparatus of claim 2, wherein the second time interval is substantially equal to a sum of $\tau$ and a time value $\Delta t$, a sum of a multiple of $\tau$ and the time value $\Delta t$, or a difference between a multiple of $\tau$ and the time value $\Delta t$, the time value $\Delta t$ being substantially equal to half of $\tau$.

4. The apparatus of claim 1, further comprising a processor configured to perform a correction of at least one of the first and second clean direct NMR echoes.

5. The apparatus of claim 4, wherein the correction is performed by applying the direct-echo pulse sequence to a calibration sample and using a plurality of clean direct NMR echoes acquired from the calibration sample, or wherein the correction is performed based on an NMR simulation.

6. The apparatus of claim 1, further comprising a processor configured to estimate at least one of a porosity value and a $T_2$ value of the formation based on the NMR echo train.

7. The apparatus of claim 1, wherein the at least one separate NMR echo train includes a first echo train acquired using a first CPMG-type sequence, the first CPMG-type sequence and the direct-echo pulse sequence having a wait time that is substantially the same.

8. The apparatus of claim 7, wherein the correction is based on an inequality between a porosity derived from the first CPMG-type sequence and a porosity derived from the direct-echo pulse sequence.

9. The apparatus of claim 8, wherein the at least one separate NMR echo train includes a second echo train acquired using a second CPMG-type pulse sequence having a wait time that is longer than the wait time associated with the first CPMG-type sequence and the direct-echo pulse sequence, and the processor is configured to correct a $T_2$ distribution obtained from the second CPMG-type pulse sequence based on the inequality.

10. A method of estimating properties of an earth formation downhole, the method comprising:
    deploying a carrier into a borehole in the earth formation;
    generating a static magnetic field in a volume of interest within the formation by a magnet assembly disposed in the carrier;
    emitting pulses of an electromagnetic signal, by at least one transmitting assembly disposed in the carrier, into the volume of interest to generate an oscillating magnetic field, the pulses emitted as a direct-echo pulse sequence having a plurality of successive pulses, the plurality of successive pulses including a first pulse and a second pulse configured to generate a first clean direct NMR echo, and a third pulse, the third pulse selected to at least partially separate a stimulated NMR echo from a second clean direct NMR echo occurring after the third pulse; and
    estimating a property of the volume of interest by a processor based on amplitudes of at least the first and second clean direct NMR echoes of an NMR echo train resulting from the pulse sequence; and
    acquiring at least one separate NMR echo train and performing a correction of NMR data associated with the at least one separate NMR echo train, the correction based on the first and second clean direct NMR echoes.

11. The method of claim 10, wherein the center of the first pulse and the center of the second pulse are separated by a first time interval $\tau$, and the center of the second pulse and the center of the third pulse are separated by a second time interval, the second time interval not substantially equal to $2\tau$.

12. The method of claim 11, wherein the second time interval is substantially equal to a sum of $\tau$ and a time value $\Delta t$, a sum of a multiple of $\tau$ and the time value $\Delta t$, or a difference between a multiple of $\tau$ and the time value $\Delta t$, the time value $\Delta t$ being substantially equal to half of $\tau$.

13. The method of claim 10, further comprising performing a correction of at least one of the first and second clean direct NMR echoes.

14. The method of claim 13, wherein the correction is performed by applying the direct-echo pulse sequence to a calibration sample and using a plurality of clean direct NMR echoes acquired from the calibration sample, or wherein the correction is performed based on an NMR simulation.

15. The method of claim 10, further comprising estimating at least one of a porosity value and a $T_2$ value of the formation based on the NMR echo train.

16. The method of claim 10, wherein the at least one separate NMR echo train includes a first echo train acquired using a first CPMG-type sequence, the first CPMG-type sequence and the direct-echo pulse sequence having a wait time that is substantially the same.

17. The method of claim 16, wherein the correction is based on an inequality between a porosity derived from the first CPMG-type sequence and a porosity derived from the direct-echo pulse sequence.

18. The method of claim 17, wherein the at least one separate NMR echo train includes a second echo train acquired using a second CPMG-type pulse sequence having a wait time that is longer than the wait time associated with the first CPMG-type sequence and the direct-echo pulse sequence, and the processor is configured to correct a $T_2$ distribution obtained from the second CPMG-type pulse sequence based on the inequality.

* * * * *